(12) United States Patent
Roth et al.

(10) Patent No.: US 6,838,081 B1
(45) Date of Patent: Jan. 4, 2005

(54) METHODS FOR ENHANCING ANTIGEN-PRESENTING CELLS AND ANTI-TUMOR RESPONSES IN A HUMAN PATIENT

(75) Inventors: Michael Derek Roth, Los Angeles, CA (US); Robert Alan Figlin, Los Angeles, CA (US); Sylvia Marie Kiertscher, Los Angeles, CA (US); Barbara Jennifer Gitlitz, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/647,248

(22) PCT Filed: Apr. 2, 1999

(86) PCT No.: PCT/US99/07376
§ 371 (c)(1),
(2), (4) Date: Nov. 17, 2000

(87) PCT Pub. No.: WO99/51257
PCT Pub. Date: Oct. 14, 1999

Related U.S. Application Data

(60) Provisional application No. 60/115,788, filed on Jan. 13, 1999, and provisional application No. 60/080,512, filed on Apr. 2, 1998.

(51) Int. Cl.[7] .................. A01N 63/00; A61K 45/00; A61K 38/19; C12N 5/01; C12N 5/08

(52) U.S. Cl. .................. 424/93.7; 424/93.71; 424/85.2; 424/85.7; 435/372; 435/355; 435/366; 435/374; 435/377; 435/384; 435/386; 435/423

(58) Field of Search .................. 424/85.2, 85.7, 424/93.1, 93.71; 435/355, 366, 374, 375, 377, 384, 386, 423

(56) References Cited
PUBLICATIONS

Romani et al. Immunological method 19965, vol. 196, pp. 137–151.*
Ambe et al S–100 Protein–positive dendritic cells in coloraectal adedenocarcinomas, Cancer 63:496–503, 1989 (Exhibit 1).
Bachettis et al.: Transfer of gene for thymidine kinase–deficient human cells by purified herpes simplex viral DNA. PNAS USA, 1977 74:1590 (Exhibit 2).
Banchereau and Steinman, Dendritic cells and the control of immunity, Nature 392:245, 1998 (Exhibit 3).
Becker Becker, Y., Anticancer role of dendritic cells (DC) in human and experimental cancers—A review, Anticancer Res. 1992, 12:511–520 (Exhibit 4).
Bernhard et al 1995 Cancer Res. 55:1099–1104 (Exhibit 5).
Bukowski et al 1993 J. Immunoth. 13:267–276 (Exhibit 6).
Caux et al., 1996, J. Exp. Medicine 184:695–206 (Exhibit 7).
Chen et al 1994 J. of Immunology 153:4775–4787 (Exhibit 8).

Enk et al 1997 Internat. J. Cancer 73:309–316 (Exhibit 9).
Flamand et al 1994 Eur. J. Immunol. 24:605–610 (Exhibit 10).
Freundenthal and Steinman 1990 PNAS 87:7698 (Exhibit 11).
Furukawa et 1985 Cancer 56:2651–2656 (Exhibit 12).
Galrilovich et al. 1997 Clin. Cancer Res. 3:483–490 (Exhibit 13).
Geller et al. an efficient deletion mutant packaging system for a defective herpes simplex virus vectors: Potential applications to human gene therapy and neuronal physiology. PNAS USA, 1990 87:8950 (Exhibit 14).
Ghosh et al 1993 Eur. Cytokine Network 4:205–211 (Exhibit 15).
Ghosh–Choudhury G, et al., Human adenovirus cloning vectors based on infectious bacterial plasmids. Gene 1986; 50:161 (Exhibit 16).
Gilleece et al 1992 Br. J. Cancer 66:204–210 (Exhibit 17).
Grabbe et al 1995 Immunology Today 16:117–120 (Exhibit 18).
Gunji et al 1997 Oncology 54:69–73 (Exhibit 19).
Hock RA, et al., Retrovirus mediated transfer and expression of drug resistance genes in human hemopoietic progenitor cells. Nature 1986; 320:275 (Exhibit 20).
Hsu et al 1996 Nature Med. 2:52–58 (Exhibit 21).
Huang et al 1994 Science 264:961–965 (Exhibit 22).
Ishigami et al 1998 Oncology 55:65–69 (Exhibit 23).
June et al 1994 Immunol. Today 15:321–331 (Exhibit 24).
Kaufman R.J.; identification of the component necessary for adenovirus translational control and their utilization in cDNA expression vectors. PNAS USA, 1985 82:689 (Exhibit 25).
Kiertscher and Roth 1996 J Leukocyte Biol. 59: 208–218 (Exhibit 26).
Lauener et al 1990 Eur. J. Immunol. 20:2375–2381 (Exhibit 27).
Markowicz et al 1990 J. Clin. Investigation 85:9955–961 (Exhibit 28).

(List continued on next page.)

Primary Examiner—James Housel
Assistant Examiner—Baoqun Li
(74) Attorney, Agent, or Firm—Mandel & Adriano

(57) ABSTRACT

The present invention provides methods for enhancing the development of APC from precursor cells by administering a combination of GM-CSF and IL-4. The precursor cells include: cells contained in peripheral blood, CD14[+] cells and precursors in bone marrow. Thus, administration of GM-CSF and IL-4 can be used as a form of cytokine immunotherapy. One embodiment of the present invention involves systemic administration of GM-CSF and IL-4. In this embodiment, APC are required to directly access tumor antigens as they exist in vivo within the patient. A further embodiment of the present invention involves co-administration of a tumor-associated or tumor-specific antigen, with GM-CSF and IL-4, to induce antigen-specific immunity mediated by APC. Yet another embodiment of the present invention describes systemic administration of GM-CSF and IL-4 to achieve reduced tumor burden.

4 Claims, 8 Drawing Sheets

OTHER PUBLICATIONS

Mayordomo et al 1995 *Nature Medicine* 1:1297–1302 (Exhibit 29).
Mehta–Damini et al 1994 *J Immunology* 153:996–1003 (Exhibit 30).
Modino and Jenkins 1994 *J. Leukocyte Biol.* 55:805–815 (Exhibit 31).
Morse et al 1997 *Ann. Surgery* 226:6–16 (Exhibit 32).
Morse et al., 1999 *Cancer Research* 59:56–58 (Exhibit 33).
Nestle et al 1998 *Nature Med.* 4:328–332 (Exhibit 34).
Ostrand–Rosenberg et al 1994 *Current Opinion in Immunology* 6:722–727 (Exhibit 35).
Peters et al 1993 *Adv. Exp. Med. Biol.* 329:275–280 (Exhibit 36).
Philips et al 1989 *Blood*: 74:26–34 (Exhibit 37).
Ratta et al., 1998 *Br J. Haematology* 101:756–65 (Exhibit 38).
Romani et al 1994 *J. Exp. Med* 180:83–93 (Exhibit 39).
Rosenfeld M, et al., Adenovirus–mediated transfer of a recombinant $\alpha_1$–antitrypsin gene to the lung epithelium in vivo. *Science* 1991; 252:431 (Exhibit 40).
Rosenzwajg et al., 1996, *Blood* 87:535 (Exhibit 41).
Sallusto et al 1994 *J. Exp. Med.* 179: 1109–1118 (Exhibit 42).
Sarver N, et al., Bovine papilloma virus DNA: A novel eukaryotic cloning vector. *Mol Cell Biol* 1981; 1:486 (Exhibit 43).
Schroder et al 1988 *Am J. Clin. Path.* 89:295–300 (Exhibit 44).
Smith et al. infectious vaccinia virus recombinants that express hepatitis B virus surface antigens. *Nature*, 1983 302:490 (Exhibit 45).
Tao and Levy 1993 *Nature* 362:755–758 (Exhibit 46).
Thomas and Lipsky 1994 *J. Immunol.* 153:4016–4027 (Exhibit 47).
Troy et al 1998 *Clin. Cancer Res.* 4:585–593 (Exhibit 48).
Wakimoto et al 1996 *Cancer Research* 56:1828–1833 (Exhibit 49).
Zhou and Tedder, 1996 *PNAS* 93:2588–92 (Exhibit 50).

Panicali D, et al., Construction of pox virus as cloning vectors: Insertion of the thymidine kinase gene from herpes simplex virus into the DNA of infectious vaccine virus. *Proc Natl Acad Sci USA* 1982; 79:4927 (Exhibit 52).
Young et al 1992 *J. Clin. Invest.* 90:229–237 9 (Exhibit 52).
Hart 1997, *Blood* 90:3245 (Exhibit 53).
Guild B, et al., Development of retrovirus vectors useful for expressing genes in cultured murine embryonic cells and hematopoietic cells in vivo. *J Virol* 1988; 62:3795–3801 (Exhibit 54).
Atkinson et al. In vivo administration of granulocyte colony–stimulating factor (G–CSF), granulocyte–macrophage CSF, interleukin–1 (IL–1), and IL–4, alone and in combination, after allogeneic murine hematopoietic stem cell transplantation. Blood. Mar. 15, 1991, vol. 77, No. 6, pp. 1376–1382. (Exhibit 55).
Berkner, K.L.: Development of adenovirus vectors for expression of heterologous genes. *Biotechniques*, 1988 6:616–624. (Exhibit 56).
Gillies, SD et al. Biological activity and in vivo clearance of antitumor antibody/cytokine fusion proteins. 1993 *Bioconj. Chem.* May–Jun.; 4:230–235. (Exhibit 57).
Iscove et al., Presursors (pre–CFCmulti) of multilineage hemopoietic colony–forming cells quantitated in vitro. The Journal of Immunology. Jul. 1, 1990, vol. 145, No. 1, pp. 190–195. (Exhibit 58).
Murphy et al. Phase I Clinical Trial: T–Cell Therapy for Prostate Cancer Using Autologous Dendritic Cells Pulsed With HLA–A0201–Specific Peptides from Prostate–Specific Membrane Antigen; 1996 *Prostate* 29:371–380. (Exhibit 59).
O'garra et al. The BCL1 B lymphoma responds to IL–4, IL–5, and GM–CSF. Cellular Immunology. 1989, vol. 123, pp. 189–200 (Exhibit 60).
Tepper et al., Experimental and clinical studies of cytokine gene–modified tumor cells. Human Gene Therapy. 1994, vol. 5, pp. 153–164. (Exhibit 61).

\* cited by examiner

METHODS FOR ENHANCING ANTIGEN-PRESENTING CELLS AND ANTI-TUMOR RESPONSES IN A HUMAN PATIENT

This application is a 371 of International Patent Application No. PCT/US99/07376, filed on Apr. 02, 1999, which claims the benefit of U.S. Provisional Application No. 60/115,788, filed on Jan. 13, 1999, and claims the benefit of U.S. Provisional Application No. 60/080,512, filed on Apr. 02, 1998.

FIELD OF INVENTION

The present invention relates generally to the field of cytokine immunotherapy, wherein a combination of granulocyte macrophage-colony stimulating factor (GM-CSF) and interleukin-4 (IL-4) are administered in vivo to human patients as a method for enhancing the development of antigen presenting precursors, functional antigen presenting cells (APC), and anti-tumor immune responses.

BACKGROUND OF THE INVENTION

APC precursors respond to appropriate cytokine signals by developing into functional APC capable of stimulating an antigen-specific immune response. Many pathways of tumor-specific immunity have been identified, but the most potent is that initiated by antigen-presenting dendritic cells (DC) and mediated by tumor-specific cytotoxic T-lymphocytes (Ostrand-Rosenberg et al 1994 *Current Opinion in Immunology* 6:722–727; Grabbe et al., 1995, *Immunology Today* 16:117).

Dendritic cells are a diverse group of morphologically and functionally similar APC present in small numbers in skin, liver, lung, spleen, blood, lymphoid organs, and bone marrow (Banchereau and Steinman 1998, *Nature* 392:245; Hart 1997, *Blood* 90:3245). The DC population is therefore complex, as it is comprised of cells at varying stages of maturation, as well as of cells derived from many different precursors (Banchereau and Steinman 1998, *Nature* 392:245; Hart 1997, *Blood* 90:3245).

In attempts to propagate and study DC in vitro, researchers have isolated either mature DC or their precursors from different sources including cord blood (Caux et al., 1996 *J. Exp. Medicine* 184:695–206), bone marrow (Ratta et al., 1998 *Br J. Haematology* 101:756–65), circulating CD34$^+$ stem cells (Rosenzwajg et al., 1996, *Blood* 87:535), and peripheral blood monocytes (Kiertscher and Roth, 1996 *J. Leukocyte Biol.* 59:208–218), and exposed them to widely different culture conditions including human serum (Kiertscher and Roth, 1996 *J. Leukocyte Biol.* 59:208–218), fetal calf serum (Caux et al., 1996 *J. Exp. Medicine* 184:695–206), and various cytokines (reviewed in Hart 1997, *Blood* 90:3245), resulting in cells that exhibit a variety of different phenotypes and functions. One question that remains to be answered is how all of these cells are related and whether or not they should all be classified as DC.

In general, APC initiate tumor-specific immunity in vivo by the following pathway: immature APC take-up and process antigen, migrate to the lymphoid organs, and develop into mature APCs that present the processed antigen to T-cells, thereby stimulating an antigen-specific immune response.

The phenotype of APC precursors isolated from peripheral blood includes cells expressing the markers CD13, CD14, and CD33, suggesting that they are myeloid in origin (Kiertscher and Roth 1996 *J Leukocyte Biol.* 59: 208–218). In contrast, the phenotype of mature APC isolated from peripheral blood exhibit minimal CD14 while expressing high levels of HLA-DR (MHC class II), co-stimulatory molecules such as CD80, CD86 (June et al 1994 *Immunol. Today;* Young et al 1992 *J. Clin. Invest.* 90:229–237; Modino and Jenkins 1994 *J. Leukocyte Biol.* 55:805–815), and other cell surface molecules including CD4, CD11c, and CD83 (Kiertscher and Roth 1996 *J. Leukocyte Biol.* 59:208–218). Functionally mature APC can be propagated in vitro, in the presence of cytokines, from CD14$^+$ precursor cells recovered from peripheral blood and from CD34$^+$ cells recovered from cord blood, cytokine-mobilized adult blood, or bone marrow. APC that develop from precursors in vitro exhibit similar phenotypic and functional characteristics to those observed with circulating APC recovered from peripheral blood, including: high levels of expression of HLA-DR; expression of CD80, CD83, and CD86; and potent antigen-presentation activity capable of stimulating antigen-specific T-cells.

The Role of APC in Stimulating Anti-tumor Immunity in Animal Models

It has been postulated that APC are capable of inducing anti-tumor immunity, and that they are absolutely essential for this process to occur (Ostrand-Rosenberg et al 1994 *Current Opinion in Immunology* 6:722–727; Grabbe et al 1995 *Immunology Today* 16:117–120; Huang et al 1994 *Science* 264:961–965). Therefore, development of APC vaccines has been extensively investigated. In an early study, the role of APC in anti-tumor immunity was demonstrated by using as few as 2×10$^5$ primed DC to induce immunity when injected into naive mice (Inaba et al 1990 *Intern. Rev. Immunol.* 6:197–206). In a later study, the unique anti-tumor activity of DC was demonstrated when mouse DC pulsed with idiotype antigen from a B-cell lymphoma were injected into naive mice. The recipient mice were effectively protected from subsequent tumor challenges, and the treatment established a state of lasting immunity. Injection of antigen alone, or B-cells pulsed with antigen had no effect, suggesting that DC were responsible for the anti-tumor immunity (Flamand et al 1994 *Eur. J. Immunol.* 24:605–610). In a different study, mice were inoculated with a CD80 transfected tumor known to produce anti-tumor immunity, and only mice with MHC-compatible APC were capable of rejecting a subsequent tumor challenge (Huang 1994 *Science* 264:961–965). As a further test of this theory, it was demonstrated that bone marrow-derived DC can be pulsed with tumor-antigens in vitro then injected into syngeneic mice as an effective anti-tumor vaccine (Mayordomo et al 1995 *Nature Medicine* 1:1297–1302).

The Role of APC as stimulators of Anti-tumor Immunity in Humans

There is evidence that APC play a similar role in inducing anti-tumor immunity in humans. Peptide-specific cytotoxic T-lymphocytes were readily induced from purified CD8$^+$ T-cells using peptide-pulsed DC, but were not induced when peptide-pulsed monocytes were used (Mehta-Damini et al 1994 *J Immunology* 153:996–1003). From a clinical perspective, four patients with advanced B-cell lymphomas were treated with DC that were recovered by density-gradient separation from their blood and pulsed with their own tumor idiotype antigen. This DC therapy resulted in a measurable reduction in the patient's B-cell lymphoma in three of the four treated patients (Hsu 1996, Nature Medicine 2:52). Similar results have been obtained using cytokine-induced DC, developed for ex vivo administration, from the peripheral blood of patients with prostate cancer and melanoma (Murphy 1996, *Prostate* 29:371; Nestle 1998, *Nature Medicine* 4:328). In both of these cases, the DC were pulsed with tumor-specific or tumor-associated antigens prior to being used as a vaccine, and reductions in tumor burden were observed in a minority of patients.

APC are Present at Low Levels in Cancer Patients

DC are limited in both number and function in human cancer patients. Immunohistological examination of renal cell cancer showed only 0.03% to 0.55% of the infiltrating leukocytes expressed the CD83 DC marker, and these cells failed to express important co-stimulatory molecules such as CD80 and CD86 (Troy et al 1998 *Clin. Cancer Res.* 4:585–593). In another study, purified CD83$^+$ DC from both regressing and progressing melanoma metastases were examined for antigen-presenting activity. The DC from regressing metastases expressed CD86 and functioned as antigen-presenting cells, but the DC recovered from progressing metastases expressed little CD86 and induced T cell anergy instead of stimulation (Enk et al 1997 *Internat. J. Cancer* 73:309–316). Similarly, DC isolated from breast cancer patients were defective, and DC function inversely correlated with tumor stage (Gabrilovich et al 1997 *Clin. Cancer Res.* 3:483–490). Histopathology studies have long reported a correlation between the number of tumor-associated DC and patient survival (Furukawa et al 1985 *Cancer* 56:2651–2656; Schroder et al 1988 *Am J. Clin. Path.* 89:295–300; Ambe et al 1989 *Cancer* 63:496–503; Becker 1992 *Anticancer Res.* 12:511–520; Ishigami et al 1998 *Oncology* 55:65–69). Although the number of DC is low in cancer patients, large numbers of functional DC can be propagated in vitro in the presence of cytokines (Nestle et al 1998 *Nature Med.* 4:328–332; Murphy et al 1996 *Prostate* 29:371–380; Morse et al 1997 *Ann. Surgery* 226:6–16; Bernhard et al 1995 *Cancer Res.* 55:1099–1104). One important approach to cancer therapy is to stimulate viable APC precursors to develop into functional APC.

The Use of Cytokines in the Development of APC Immunotherapy

The development of DC immunotherapy for the treatment of human cancer has been a subject of intense study. However, several factor have limited DC research in the past, including DC rarity and the extensive immunoselection techniques required to recover them (Freundenthal and Steinman 1990 *PNAS* 87:7698; Thomas and Lipsky 1994 *J. Immunol.* 153:4016–4027; Kiertscher and Roth 1996 *J. Leukocyte Biology* 59:208–218). A major factor that has limited APC immunotherapy is the exceptionally rare frequency of mature APC in blood, where they constitute only 0.05% to 0.3% of the circulating mononuclear cells (Grabbe 1995 *Immunology Today* 16:117–120; Kiertscher and Roth et al 1996 *J. Leukocyte Biology* 59:208–218). However, new techniques now allow cytokines to be used in vitro to propagate large numbers of APC from peripheral blood (Romani et al 1994 *J. Exp. Med* 180:83–93). The combination of GM-CSF and IL-4 induces peripheral blood monocytes to differentiate into APC, resulting in a 100-fold amplification in the yield of dendritic APC in vitro (Kiertscher and Roth 1996 *J. Leukocyte Biol.* 59:208–218).

Recent immunotherapy methods have attempted to develop DC vaccines to treat human cancers. In several clinical trials, GM-CSF was used in combination with either IL-4 or TNFα to propagate DC in vitro from cells isolated from the patient's blood, the DC were loaded with tumor antigen of interest, then used to vaccinate patients with either B cell lymphoma (Hsu et al 1996 *Nature Med.* 2:52–58), melanoma (Nestle et al 1998 *Nature Med.* 4:328–332), or prostate cancer (Murphy et al 1996 *Prostate* 29:371–380). Anti-tumor immunity and objective clinical responses were observed in all of the studies. Although DC immunotherapy using ex vivo generated DC has been extensively studied, it may not be the most practical method to treat cancer patients. Blood must be drawn from the patient, manipulated in vitro to enrich the population of DC, and then administered back to the patient. This method presents the risk of contamination of the sample, and requires a facility dedicated to precursor cell enrichment and sterile manipulation of blood samples. This approach is limited by the amount of blood that can be safely drawn from the patient, or requires invasive leukophoresis techniques to extract precursor cells. In addition, little is known about the appropriate site or route of vaccination to optimize DC development, as intravenous and subcutaneous administration result in no detectable DC in the lymphoid organs or tumor site (Morse et al., 1999 *Cancer Research* 59:56–58).

GM-CSF and IL-4 Induces Differentiation of Potent APC in vitro

The combination of GM-CSF and IL-4 promotes differentiation of peripheral blood mononuclear cells (PBMC) into APC in vitro (Romani et al 1994 *J. Exp. Med.* 180:83–93; Sallusto et al 1994 *J. Exp. Med.* 179:1109–1118). More specifically, it has been demonstrated that CD14$^+$ monocytes are the peripheral blood precursors that mature into DC that exhibit antigen-presenting activity (Kiertscher et al 1996 *J. Leukocyte Biol.* 59:208–218; Zhou and Tedder, 1996 *PNAS* 93:2588–92). GM-CSF is an independent trophic factor for both monocytes and DC (Markowicz et al 1990 *J. Clin. Investigation* 85:9955–961), while IL-4 primarily induces maturation along the DC developmental pathway (Peters et al 1993 *Adv. Exp. Med. Biol.* 329:275–280). GM-CSF provides the primary proliferative signal. In contrast, IL-4 induces myeloid precursors to decrease the expression of CD14 (Lauener et al 1990 *Eur. J. Immunol.* 20:2375–2381) with a concomitant increase in the expression of important antigen-presenting molecules, such as HLA-DR, CD80, CD86, and CD40 (Kiertscher and Roth; FIG. 1A). The effect of GM-CSF and IL-4 are synergistic, as the presence of both cytokines is required for in vitro transformation of DC precursor cell into mature APC (Sallusto et al 1994 *J. Exp. Med.* 179:1109–1118).

Antigen-presenting Phenotype and Activity is Dose and Time Dependent Upon the Combination of GM-CSF and IL-4: in vitro studies The in vitro administration of GM-CSF in combination with IL-4 induced the development of APC from PBMC, in a dose and time-dependent manner. Adherent peripheral blood mononuclear cells were cultured in a fixed amount of GM-CSF and either no or increasing amounts of IL-4. The combination of GM-CSF and higher amounts of IL-4 are required to induce the development of APC having the following characteristic: an increase in the expression of important antigen-presenting molecules, such as HLA-DR, CD80, and CD86; a dose-dependent increase in endocytotic activity as measured by the capacity of the cells to take-up FITC-labeled dextran; and an increase in the capacity to present soluble antigens and stimulate antigen-dependent T cell responses. Thus, GM-CSF and IL-4 act synergistically to induce antigen-presenting activity that is up to 20 times greater than that observed with either cytokine alone.

SUMMARY OF THE INVENTION

The present invention provides methods for enhancing the development of APC from precursor cells by administering a combination of GM-CSF and IL-4. The precursor cells include: cells contained in peripheral blood, CD14$^+$ cells and precursors in bone marrow. Thus, administration of GM-CSF and IL-4 can be used as a form of cytokine immunotherapy. One embodiment of the present invention involves systemic administration of GM-CSF and IL-4. In this embodiment, APC are required to directly access tumor antigens as they exist in vivo within the patient. A further embodiment of the present invention involves co-administration of a tumor-associated or tumor-specific antigen, with GM-CSF and IL-4, to induce antigen-specific immunity mediated by APC. Yet another embodiment of the present invention describes systemic administration of GM-CSF and IL-4 to achieve reduced tumor burden.

BRIEF DESCRIPTION OF THE FIGURES

FIG. 6: Graph showing that cells expressing CD83 did not express CD14, but expressed high levels of HLA-DR and CD1a.

DETAILED DESCRIPTION OF THE INVENTION

Definitions

Figure 1:
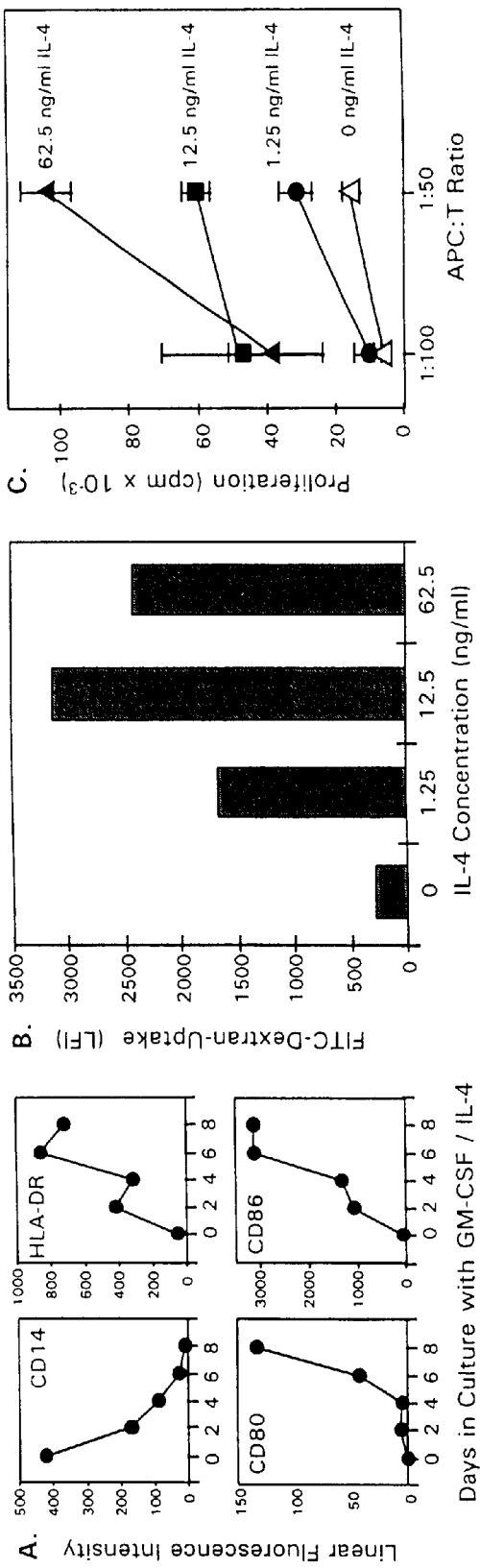
FIGS. 1A, B, C: Graphs demonstrating that APC develop from CD14-expressing peripheral blood precursors in vitro in a time- and dose-dependent manner in response to GM-CSF and IL-4.

As used in this application, the following words or phrases have the meanings specified.

The term "administering" used herein is defined to mean either the direct or indirect delivery of the chemical compounds GM-CSF and IL-4.

The term "enhancing" used herein is defined to include: an increase in cell number, and/or biologic characteristics described therein.

The term "development" used herein is defined to include: proliferation, differentiation and/or maturation.

The phrase "antigen presenting precursor cells" used herein is defined to include: cells capable of developing into cells that exhibit the characteristics of antigen presenting cells.

The phrase "antigen presenting cells" is used herein to include cells that exhibit characteristics including: the expression of cell surface proteins involved in the process of antigen presentation (for example HLA-DR, CD80 and CD86), endocytotic activity, and the ability to stimulate antigen-specific proliferation of T-cells.

The phrase "tumor specific immune response" used herein is defined to include an immune response stimulated by antigen presenting cells in conjunction with a tumor-associated or tumor-specific antigen.

The terms "granulocyte macrophage-colony stimulating factor (GM-CSF)" and "interleukin-4 (IL-4)" used herein are defined to include natural or recombinant proteins of any composition, or the genes encoding such proteins that bind and exert biological function at the human GM-CSF and IL-4 receptors, respectively.

The following examples are presented to illustrate the present invention and to assist one of ordinary skill in making and using the same. The examples are not intended in any way to otherwise limit the scope of the invention.

The present invention provides a method for administering GM-CSF and IL-4 in an amount and for a time sufficient to promote proliferation, differentiation and/or maturation of the precursor cells into antigen-presenting cells, e.g. in a human. The appearance of circulating antigen-presenting precursor cells and APC can be monitored by phenotypic and clinical features which will be discussed below and in more detail in sections that follow.

The Type of GM-CSF and IL-4

In the practice of the invention, both glycosylated and unglycosylated forms of GM-CSF and IL-4 can be administered. Also, recombinant human GM-CSF and IL-4 can be administered. The invention also contemplates administering natural purified forms of GM-CSF and IL-4.

Administering Dosage and Duration of GM-CSF and IL-4 Therapy

The present invention provides a method for administering the combination of GM-CSF and IL-4 in an amount and for a time sufficient to promote proliferation, differentiation and/or maturation of the precursor cells into antigen-presenting cells, in a human.

Systemic administration of GM-CSF produces predictable patient response, as the dose-response and clinical toxicity of GM-CSF has been established (Philips et al 1989 *Blood:* 74:26–34; Bukowski et al 1993 *J. Immunoth.* 13:267–274). A two-week course using GM-CSF induced a 5 to 20-fold increase in the number of circulating $CD14^+$ cells, and was well tolerated. A relatively low daily dose of about 2.5 ug/kg/day of GM-CSF avoided the potential side effects of higher dose therapy.

Systemic administration of IL-4 also produces predictable results. The maximum tolerated dose of IL-4 has been reported to be about 5 $\mu$g/kg/day when given as a daily two week course of treatment (Gilleece et al 1992 *Br. J. Cancer* 66:204–210). Single-dose pharmacokinetics shows that systemic levels in the range of 1 to 12 ng/ml are achieved following a single 4 $\mu$g/kg/day injection and that peak levels persist for up to 8 hours (Ghosh et al 1993 *Eur. Cytokine Network* 4:205–211). Despite the prior use of GM-CSF and IL-4 as monotherapies, there has been no report that such treatment enhances the development of APC. This parallels the results from in vitro studies that demonstrated that both cytokines must be administered to obtain optimal amplification and differentiation of mature APC.

The Mode of Administering GM-CSF and IL-4

The present invention provides a method for administering GM-CSF and IL-4 to a human patient simultaneously or substantially simultaneously. A method is also provided for administering GM-CSF and IL-4 sequentially, by administering one of the cytokines first and the other second. Additionally, a method is provided for administering GM-CSF and IL-4 by standard parenteral routes, such as subcutaneously, intravenously, or intramuscularly. Administration can be performed daily as a single dose, multiple dose, or in continuous dose form. Administration can be at the tumor site. The present invention also contemplates that GM-CSF and IL-4 can each be administered by different modes. As is standard practice in the art, GM-CSF and IL-4 can be administered with an appropriate carrier or by delivery of the genes encoding for GM-CSF and IL-4.

Other Methods for in vivo Delivery of the Cytokines of the Invention

The present invention involves direct administration of the combination of GM-CSF and IL4 to human patients. Alternative methods for in vivo delivery of the cytokines of the invention include, but are not limited to, localized injection at a specific site, administration by implantable pump or continuous infusion, injection of modified cytokines, liposomes, gene therapy, or gene-modified tumor vaccines.

The development of gene-modified tumor vaccines demonstrate that local in vivo production of both GM-CSF and IL-4 by genetically-engineered tumor cells can induce anti-tumor immune responses in mice (Wakimoto et al 1996 *Cancer Research* 56:1828–1833; Gunji et al 1997 *Oncology* 54:69–73). Results showed that only the combinations of GM-CSF and IL-4, as well as GM-CSF and TNFα significantly increased animal survival. The authors of these studies did not examine the effect of their gene-modified tumor vaccine on antigen presenting cell phenotype or function. However, the results indirectly suggest the involvement of antigen-presenting cells. In both studies, neither GM-CSF nor IL-4 alone resulted in anti-tumor immune response. Thus, gene-modified tumor vaccines provide a method for in vivo delivery of cytokines. However, the disadvantages of applying gene-modified tumor immunotherapy to treat human cancer include: difficulties with obtaining, growing and gene modifying human tumor cells from patients, and difficulty in regulating the level of cytokine expression.

An alternative method of in vivo cytokine delivery involves administering fusion proteins containing a tumor idiotype linked on the same molecule to a cytokine. The rationale behind this approach is that the idiotype from B-cell lymphoma is a weak immunogen, and fusing the idiotype to a cytokine molecule would create a stronger immunogen, and the cytokine would induce an idiotype-specific immune response. In two studies using the murine model, fusion proteins containing idiotype from mouse B-cell lymphoma linked to either GM-CSF, (Tao and Levy 1993 *Nature* 362:755–758) IL-2, or IL-4 (Chen et al 1994 *J. of Immunology* 153:4775–4787) were used to immunize mice against a subsequent tumor challenge. The results showed that tumor protection was specific for the B-cell idiotype contained on the fusion protein. To date, attempts to use an admixture of fusion proteins carrying GM-CSF and IL-4 has not been reported. Another study using fusion proteins containing anti-ganglioside Ab linked to either IL-2 or GM-CSF showed a significant reduction in bioactivity of the GM-CSF containing fusion protein, presumably because the potential conformation of the GM-CSF linked to this particular idiotype rendered the cytokine less active (Gillies et al 1993 *Bioconj Chem.* 4:230). Thus, the disadvantage of using fusion proteins for cytokine immunotherapy in humans, is that it may not be a reliable method due to the unpredictable nature of the conformational changes of the fusion protein that could lead to diminished bioactivity of the cytokines.

In vivo Administration of GM-CSF and IL-4 to Amplify Circulating APC

The present invention provides methods for enhancing the development of APC from precursor cells by administering a combination of GM-CSF and IL-4. One embodiment of the present invention involves systemic administration of the combination of GM-CSF and IL-4. The effects of systemic administration of GM-CSF and IL-4 has been tested, using a fixed dose of GM-CSF in combination with no or increasing amounts of IL-4. In general, the results demonstrate that GM-CSF in combination with the higher doses of IL-4 produced the most positive results. Clinical response to this cytokine therapy included a patient with prostate cancer that experienced a reduction in tumor size, and a reduction in serum prostate specific antigen (PSA) levels, consistent with a partial anti-tumor response. Systemic administration of GM-CSF and IL-4 also induced an increase in the number of circulating $CD14^+$ and $CD83^+$ cells, and induced an increase in the level of expression of cell markers that are associated with APC, such as HLA-DR, CD11c and CD1a. Furthermore, systemic cytokine therapy induced the development of a population of circulating cells that exhibited functional characteristics of APC, including the ability to endocytose and the ability to stimulate the antigen-specific proliferation of T-cells.

When the administration of GM-CSF and IL-4 is systemic, advantages of the present invention include the reliable systemic administration of cytokines, predictable biological responses by patients, in some cases, the ability to administer treatment as a home therapy, and rapid applicability to a wide variety of cancer patients without the requirement for invasive procedures or technologically-specialized facilities. Further, systemic administration of a combination of cytokines to the patient in order to promote the development of APC in vivo can forego the need to withdraw blood and any contamination risk associated with ex vivo DC immunotherapy. Systemic administration of cytokines also allows access to a much larger population of APC precursors than exists in an ex vivo sample of blood, and potentially allows DC to mature directly within tissues, tumors and lymphoid organs.

In another embodiment, GM-CSF and IL-4 are administered to a subject by gene therapy. In this embodiment, vectors can be used to carry functional GM-CSF and IL4 genes to the target site.

Suitable vectors for use in gene therapy include adenoviruses, lentiviruses, retroviral vectors, and adeno-associated viral (AAV) vectors.

The viral vector selected should meet the following criteria: 1) the vector must be able to infect the a target cell and thus vectors having an appropriate host range must be selected; 2) the transferred gene (i.e., GM-CSF and IL-4 genes) should be capable of persisting and being expressed in the cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles (Bachettis et al.: Transfer of gene for thymidine kinase-deficient human cells by purified herpes simplex viral DNA. *PNAS USA,* 1977 74:1590; Berkner, K. L.: Development of adenovirus vectors for expression of heterologous genes. *Biotechniques,* 1988 6:616; Ghosh-Choudhury G, et al., Human adenovirus cloning vectors based on infectious bacterial plasmids. *Gene* 1986; 50:161; Hag-Ahmand Y, et al., Development of a helper-independent human adenovirus vector and its use in the transfer of the herpes simplex virus thymidine kinase gene. *J Virol* 1986; 57:257; Rosenfeld M, et al., Adenovirus-mediated transfer of a recombinant ($\alpha_1$-antitrypsin gene to the lung epithelium in vivo. *Science* 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; identification of the component necessary for adenovirus translational control and their utilization in cDNA expression vectors. *PNAS USA,* 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduced genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. *PNAS USA,* 1990 87:8950).

Another vector for mammalian gene transfer is the bovine papilloma virus-based vector (Sarver N, et al., Bovine papilloma virus DNA: A novel eukaryotic cloning vector. *Mol Cell Biol* 1981; 1:486).

Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. *Proc Natl Acad Sci USA* 1982; 79:4927; Smith et al. infectious vaccinia virus recombinants that express hepatitis B virus surface antigens. *Nature,* 1983 302:490.)

Retroviruses are packages designed to insert viral genes into host cells (Guild B, et al., Development of retrovirus vectors useful for expressing genes in cultured murine embryonic cells and hematopoietic cells in vivo. *J Virol* 1988; 62:795; Hock R A, et al., Retrovirus mediated transfer and expression of drug resistance genes in human hemopoietic progenitor cells. *Nature* 1986; 320:275).

The basic retrovirus consists of two identical strands of RNA packaged in a proviral protein. The core surrounded by a protective coat called the envelope, which is derived from the membrane of the previous host but modified with glycoproteins contributed by the virus.

Monitoring the Appearance of Circulating Antigen-presenting APC

Peripheral blood samples from patients administered GM-CSF and IL-4 are collected serially and analyzed for expression of cell surface markers indicative of antigen-presenting cells. The cell surface markers can be monitored by FACS analysis using fluorochrome-conjugated mAb to the following mAb: anti-CD1a, -CD3,-CD4, -CD11, -CD11c, -CD13, -CD14, -CD15, -CD16, -CD20, -CD24, -CD34, CD40, -CD57, -CD80, -CD83, -CD86, and HLA-DR. This list of mAb is intended to be exemplary of possible APC and non-APC surface markers. Cells expressing CD14 in conjunction with APC markers would represent immature monocyte-derived APC developing along the DC pathway, while cells expressing CD83, but not CD14, in conjunction with APC markers would represent either stem cell derived DC or functionally-matured monocyte-derived DC.

Monitoring the Function of APC

The function of APC, generated by administration of GM-CSF and IL-4 may be monitored by their ability to take-up and present antigens, including the uptake of antigens by macropinocytosis (for example lucifer-yellow) and/or receptor-mediated endocytosis (for example FITC-labeled dextran), the presentation of soluble antigens to autologous T cells (for example TT peptide) or their ability to stimulate a MLR. This list is intended to be exemplary of possible APC functional assays and is not intended to exclude other assays which measure the described functions.

The following examples are presented to illustrate the present invention and to assist one of ordinary skill in making and using the same. The examples are not intended in any way to otherwise limit the scope of the invention.

EXAMPLES

Example 1

Clinical Protocol Using GM-CSF and IL-4

Patients were treated with daily subcutaneous injections of sterile and preservative-free human recombinant GM-CSF (specific activity=1.125×10$^7$ U/mg) and IL-4 (specific activity=2.414×10$^7$ U/mg) both provided by Schering-Plough Research Institute, Kenilworth, N.J. The 28-day protocol included 14 days of therapy followed by 14 additional days of observation; except cohort E in which patients received 7 days of therapy, followed by 7 days of rest, followed by 7 days of therapy, followed by 7 additional days of observation. After a period of instruction, injections were self-administered subcutaneously to the skin in the thigh and/or abdomen as a home-based therapy. Patients were recruited into a total of 6 successive treatment cohorts (AI, AII, B, C, D, and E) in a serial manner. Patients in cohort AI received a fixed dose of 2.5 µg/kg/day GM-CSF, while patients in subsequent cohorts received the same dose of GM-CSF in combination with IL-4 at 0.5 µg/kg/day (cohort AII), 1.0 µg/kg/day (cohort B), 2.0 µg/kg/day (cohort C), 4.0 µg/kg/day (cohort D), or 6.0 µg/kg/day (cohort E). Patients were monitored twice weekly for evidence of toxicity according to the National Cancer Institute Common Toxicity Criteria.

Example 2

Clinical Response to Administration of GM-CSF and IL-4

Figure 8:
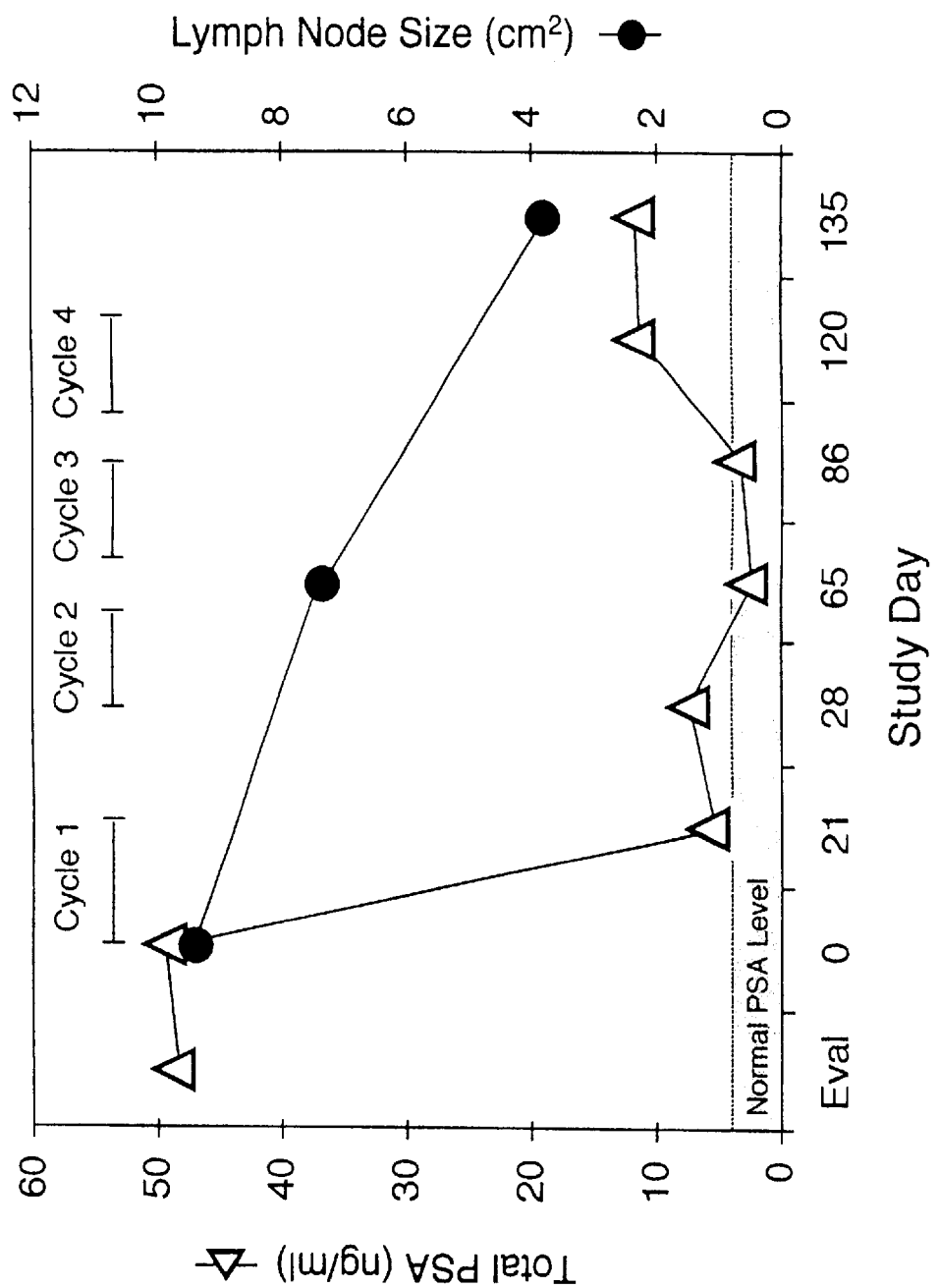
FIG. 8: Graph showing clinical responses to GM-CSF and IL-4 inpatient D2. Total prostate specific antigen (PSA, ng/ml) was monitored as a tumor marker.

The present invention provides a method for reducing tumor burden by administering GM-CSF and IL-4. All patients were assessed for changes in tumor burden associated with cytokine therapy. To date, of the 16 patients evaluable for response, one experienced a partial anti-tumor response (patient D1, enrolled in cohort D). Patient D1 had hormone-refractory prostate cancer metastatic to two mediastinal lymph nodes and multiple bones as confirmed by CT scans, bone scans, and PET scans. This patient was treated with four 14-day cycles of GM-CSF (2.5 µg/kg/day) in combination with IL-4 (4.0 µg/kg/day). Representative results for the D cohort, patient D2. Top set of graphs represents cells prior to administration of GM-CSF and IL4. Bottom set of graphs represents cells treated with GM-CSF and IL-4. This patient experienced a marked improvement in bone pain and a dramatic decrease in serum prostate specific antigen (PSA) following the first course of therapy that remained low over three subsequent cycles (FIG. 8). Furthermore, serial CT scans of the chest documented a progressive reduction in mediastinal lymph node size from an initial measurement of 9.42 cm$^2$ (greatest cross-sectional length×width) to a final measurement of 3.88 cm$^2$, meeting the criteria for a partial response (FIG. 8). Thus, administering GM-CSF and IL-4 to a patient with prostate cancer resulted in reduced tumor burden characterized by decreased levels of serum PSA and reduced tumor size.

Example 3

In vitro Generation of Antigen Presenting Cells Using GM-CSF and IL-4; Analysis of Cell Marker Phenotype The present invention provides a method for enhancing the development of antigen presenting precursor cells and functional antigen presenting cells by the administration of the combination of GM-CSF and IL-4. The effect of cytokine treatment on antigen presenting precursor cells in peripheral blood were determined in vitro by exposing adherent peripheral blood mononuclear cells (PBMC) to GM-CSF alone or in combination with IL-4. PBMC from healthy donors were prepared by Ficoll-Hypaque density gradient separation from the peripheral blood and allowed to adhere to plastic tissue culture flasks for 2 hours in complete medium (CM) containing 10% human AB serum. The non-adherent cells were gently removed by rinsing and the remaining adherent PBMC were cultured in CM containing GM-CSF alone, at 100 ng/ml, or in combination with titrating amounts of IL-4 at 1.25, 12.5, or 62.5 ng/ml. CM was composed of RPMI-1640 supplemented with glutamine (Irvine Scientific, Irvine, Calif.), 0.01 M Hepes buffer, antibiotic-antimycotic mixture (Life Technologies, Grand Island, N.Y.), and 10% heat-inactivated human AB serum (Gemini Bioproducts, Inc., Calabasas, Calif.). The cultured cells were evaluated for the development of functional antigen presenting activity, including: cell marker phenotype, endocytotic activity, and antigen presentation activity.

In order to determine the kinetics associated with cytokine-induced development of functional APC, the cells were cultured for 0, 2, 4, 6, or 8 days, then harvested after various days of culture and evaluated for expression of cell surface markers by FACS. The cell markers tested included: fluorochrome-conjugated mAbs anti-CD14, anti-CD15 (from Caltag Laboratories, South San Fransisco, Calif.), anti-HLA-DR and anti-CD80 (from Becton Dickinson, San Jose, Calif.), anti-CD11c and anti-CD86 (from PharMingen, San Diego, Calif.), anti-CD1a (from Serotec, Raleigh, N.C.), and anti-CD83 (from Coulter/Immunotech, Westbrook, Me.). The development of APC was associated with a time-dependent change in the expression of several cell surface markers, including a decrease in the level of expression of CD14 and a concurrent increase in the expression of HLA-DR, CD80 and CD86 (FIG. 1A). An increase in the expression of CD40 and CD11c were also observed. The development of APC required 6 to 8 days.

Exposure to the combination of GM-CSF and IL-4 also produced a dose-dependent increase in endocytotic activity. Adherent PBMC cultured for 7 days in CM containing GM-CSF alone (100 ng/ml) or in combination with IL-4 at 1.25, 12.5 or 62.5 ng/ml, were depleted of contaminating B cells, T cells and NK cells by incubating with specific murine monoclonal antibodies (anti-CD20, anti-CD3, and anti-CD14, respectively) followed by immunomagnetic depletion using magnetic beads coated with anti-mouse immunoglobulin antibody (Dynal M450 beads, Dynal Inc., Lake Success, N.Y.) and a magnet (as described in Kiertscher and Roth 1996, *Journal of Leukocyte Biology*, 59:208). Purified APC were then incubated with FITC-labeled dextran (MW 40,000, Molecular Probes, Eugene, Oreg.) at a concentration of 1 mg/ml for 1 hour at either 37° C. or 0° C., washed, and analyzed for the uptake of the FITC label by FACS analysis. The capacity for receptor-mediated uptake of FITC-dextran was minimal in cells cultured in GM-CSF alone, but increased in a dose-responsive manner in cells cultured in combination with IL-4 at 1.25 and 12.5 ng/ml (FIG. 1B). No further increase in FITC-dextran uptake was observed at IL4 concentrations of 62.5 ng/ml. These results demonstrate a dose-responsive increase in endocytosis in response to GM-CSF in combination with IL-4.

Furthermore, the combination of GM-CSF and IL-4 produced a dose-dependent increase in antigen presenting activity. Adherent PBMC were cultured for 7 days in CM containing GM-CSF alone or in combination with IL-4, and were evaluated for their relative ability to process and present recombinant tetanus toxin fragment C (TT from Boehringer-Mannheim Corp., Indianapolis, Ind.) to autologous T-cells (methods as described in Kiertscher and Roth, 1996 *Journal of Leukocyte Biology*, 59:208). Purified DC were pulsed with 40 µg/ml of TT and co-culture with 10$^5$ autologous T-cells for 6 days at the following APC:T-cell ratios: 1:100 and 1:50. The results demonstrated that GM-CSF alone was ineffective at inducing APC development, and that the addition of IL-4 resulted in a dose-dependent increase in antigen presenting activity (FIG. 1C).

These results demonstrated that in vitro administration of GM-CSF in combination with higher doses of IL-4 induced the development of APC from PBMC, in a dose and time-dependent manner. The cytokine-induced APCs have biologic characteristics of dendritic APCs, namely: cell surface phenotype, increased antigen presentation activity and endocytosis function. Both GM-CSF and IL-4 act synergistically to induce the development of dendritic APCs in a dose and time-dependent manner.

Example 4:

Detailed Phenotypic Analysis of CD14$^+$ Antigen Presenting Cells Generated in vivo The present invention provides a method for enhancing the development of APC from CD14$^+$ cells by administering GM-CSF and IL-4. The effects of systemic administration of GM-CSF and IL-4 on cell number and cell marker phenotype was analyzed. Peripheral blood leukocytes were collected from patients enrolled in all six cohorts (see example 1 above for description of cohorts) on days 0, 7, 14 and 21, then enriched for leukocytes by density gradient centrifugation. The cells were stained with fluorescent-labeled anti-CD 14 and the percentage of cells expressing CD14 was determined by FACS. This percentage was multiplied by the number of leukocytes recovered/ml of blood to determine the number of CD14$^+$ cells/ml of blood. * p$\leq$0.05 compared to the same cohort on day 0, paired t test. ‡p$\leq$0.05 compared to cohorts AII and B on the same day, unpaired t test.

Figure 2:
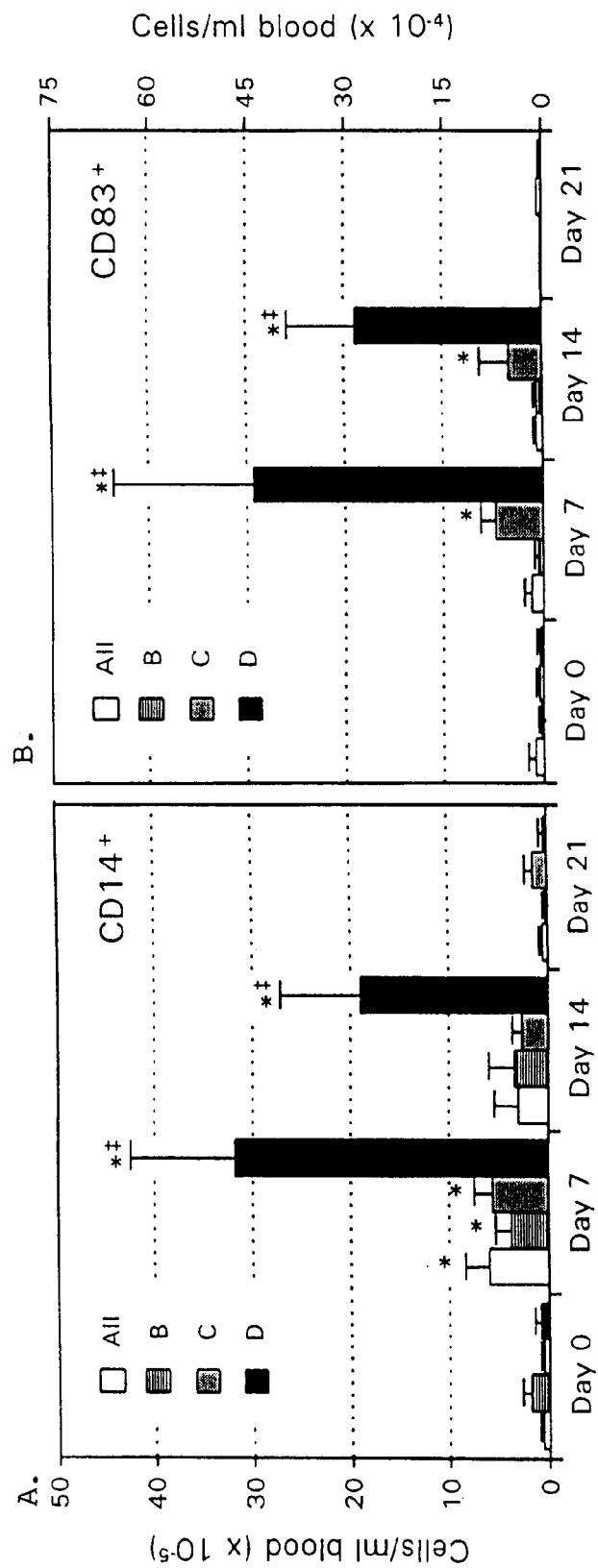
FIGS. 2A, B: Graphs demonstrating that in vivo exposure to GM-CSF and 4IL4 promotes a dose-dependent increase in the number of circulating $CD14^+$ and $CD83^+$ cells.

The administration of the combination of GM-CSF and IL-4 resulted in a dose and time-dependent increase in the number of CD14$^+$ cells (FIG. 2A). The administration of GM-CSF as a single agent for 14 days resulted in an increase in the number of circulating CD14$^+$ cells that peaked on day 7 (average 6.29×10$^5$ cells/ml, range 0.75 to 17.4×10$^5$ cells/ml) and returned to baseline levels by day 21 (average 3.5×10$^4$ cell/ml, range 0.4 to 6.7×10$^4$ cells/ml). A similar result occurred when lower doses of IL-4 was administered in combination with GM-CSF (cohorts AII, B, and C; FIG. 2A). However, increasing the IL-4 dose to 4.0 $\mu$g/kg/day resulted in a statistically significant increase in the number of circulating CD14$^+$ cells beyond that observed with GM-CSF alone (cohort D; FIG. 2A). On day 7, the number of CD14$^+$ cells averaged 6-fold higher in cohort D (average 3.2×10$^6$ cell/ml, range 0.35 to 56×10$^6$ cells/ml) compared to the cells collected from patients treated with GM-CSF alone (cohort AI). The number of CD14$^+$ cells returned to baseline by day 21. These results demonstrated that systemic administration of GM-CSF in combination with higher doses of IL-4 induced an increase in the number of circulating CD14$^+$ cells, in a dose and time-dependent manner.

Administration of the combination of GM-CSF and IL-4 also resulted in a dose and time-dependent decrease in the level of expression of CD14, as exhibited by a decrease in the intensity of CD14 staining (Table 1). This effect was detectable on day 7 in cohort C and was statistically significant at both days 7 and 14 in cohort D. Peripheral blood was collected from day 0, 7, 14 and 21 then enriched for leukocytes by density gradient centrifugation and analyzed for expression of CD14 and CD15 by FACS.

Figure 3:
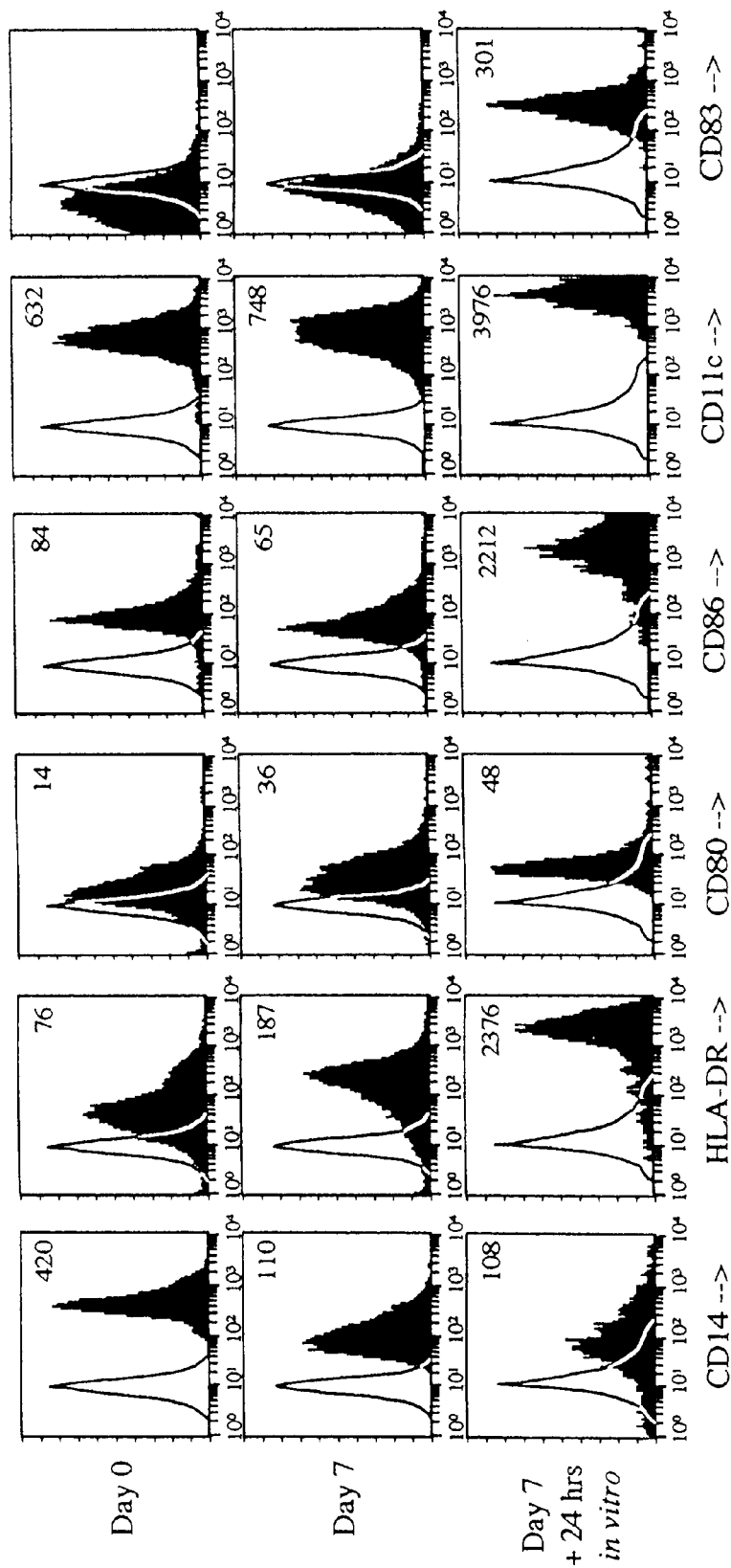
FIG. 3: Graphs demonstrating that in vivo exposure to GM-CSF and IL-4 decreased the expression of CD14 and increased the expression of HLA-DR, B7-1 and CD11c on circulating $CD14^+$ cells, and that these cells rapidly developed the phenotype of antigen presenting dendritic cells when cultured in vitro. Representative results for the E cohort, patient E4.

Cells expressing CD14 were subsequently analyzed for their relative expression of CD14, HLA-DR, CD11c, CD80, CD86, CD11c and CD83. FIG. 3 shows representative results from the E cohort, patient E4; numbers represent relative mean linear fluorescent intensity after subtracting the value obtained from unstained CD14$^+$ cells. The change in cell marker phenotype is similar to that seen for administration of both cytokines in vitro. This effect was detectable on day 7 in the C cohort and was statistically significant at both days 7 and 14 in the D cohort. The decrease in CD14 staining was concurrent with an increase in the expression of HLA-DR, CD80 and CD11c (FIG. 3, compare day 0 results with day 7 results) which was not observed in patients receiving GM-CSF alone, and was present occasionally in patients receiving less that 2 $\mu$g/kg/day of IL-4. However, unlike the results seen in vitro, the expression of CD80 increased only modestly in patients treated with GM-CSF and IL-4, and the expression of CD86 did not increase at all. These results demonstrated that systemic administration of GM-CSF in combination with higher doses of IL4 induced development of circulating APC and/or APC precursors that have cell surface phenotype characteristic of APCs, specifically: a decrease in the level of expression of CD14 and an increase in the expression of cell surface proteins involved in the process of antigen presentation.

In another analysis, cells were collected from patients after 7 days of treatment with GM-CSF and IL-4 and then cultured in RPMI-1640 medium supplemented with 10% human AB serum, devoid of cytokines, for 24 hours prior to analysis (FIG. 3; day 7+24 hrs in vitro). Results showed a rapid increase in expression of HLA-DR, CD80, CD86 and CD11c, to a magnitude similar to that observed on APC generated in vitro from adherent PBMC exposed to GM-CSF and high doses of IL-4 for 7 days. The rapid phenotypic maturation suggests that these circulating cells are immature, and then mature rapidly when they exit the circulation to enter tissues and/or lymphoid organs.

TABLE 1

CD14 expression in down-regulated by
GM-CSF in combination with increasing doses of IL-4

| | Linear Fluorescence Intensity for CD14 Expression* | | | |
|---|---|---|---|---|
| Cohort | Day 0 | Day 7 | Day 14 | Day 21 |
| AI | 1,193 ± 312 | 911 ± 35 | 1,025 ± 231 | 1,017 ± 221 |
| AII | 1,181 ± 336 | 1,503 ± 203 | 1,489 ± 181 | 1,302 ± 200 |
| B | 1,770 ± 454 | 1,284 ± 203 | 1,300 ± 301 | 1,998 ± 259 |
| C | 1,908 ± 194 | 982 ± 128$^{\|}$ | 1,299 ± 114 | 1,536 ± 143 |
| D | 1.782 ± 96 | 692 ± 50$^{\ddagger}$ | 717 ± 53$^{\ddagger}$ | 1,695 ± 320 |

*Average ± SEM for each cohort. n = 3 for cohort AI and n = 4 for cohorts AII, B, C & D.
$^{\ddagger}$p $\leq$ 0.05 compared to day 0 for the same cohort, paired t-test
$^{\|}$p $\leq$ 0.10 compared to day 0 for the same cohort, paired t-test Example 5

Figure 5:
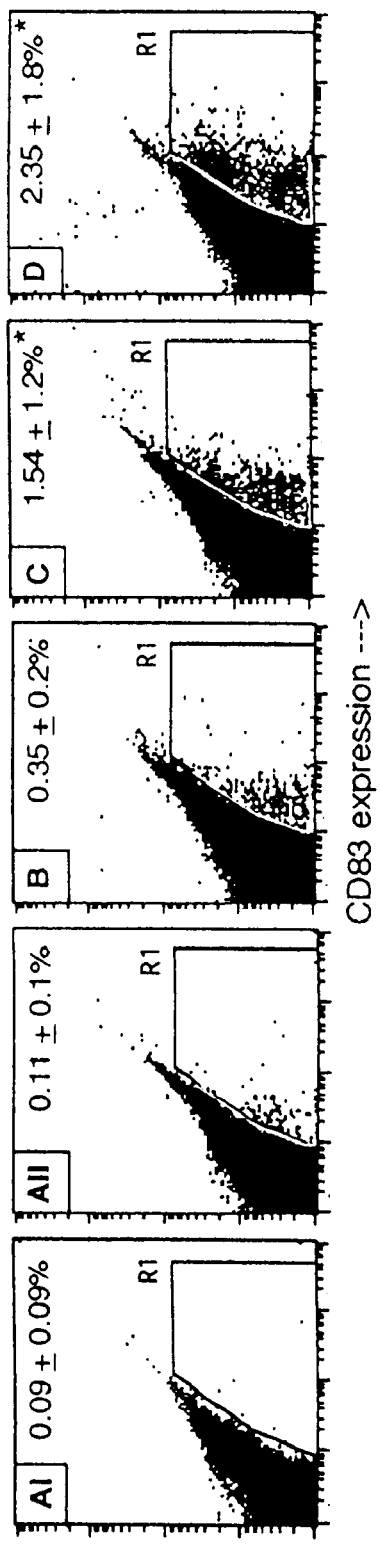
FIG. 5: Graphs showing that in vivo exposure to GM-CSF and IL-4 promoted a dose-responsive increase in the percentage of PBMC expressing CD83.

Detailed Phenotypic Analysis of CD83$^+$ Antigen Presenting Cells Generated in vivo The present invention also provides a method for enhancing the development of APC expressing CD83 by administering GM-CSF and IL-4. Previous studies by others have demonstrated that both GM-CSF and IL,4 are required to induce development of APC from stem cells in vitro (Sallusto et al 1994 *J. Exp. Med.* 179: 1109–1118). This pathway of DC maturation is associated with the early expression of several markers, including CD83 and CD1a that are only expressed on CD14-derived DC at terminal stages in their development. This pathway was monitored by collecting leukocytes from patients enrolled in all six cohorts on days 0, 7, 14 and 21 (FIG. 2B). The cells were stained with fluorescent-labeled anti-CD83 and anti-HLA-DR mAb and analyzed by FACS. This percentage was multiplied by the number of leukocytes recovered/ml of blood to determine the number of CD83$^+$/HLA-DR$^+$ cells/ml of blood. * p $\leq$0.05 compared to the same cohort on day 0, paired t test. ‡p$\leq$0.05 compared to cohorts AII and B on the same day, unpaired t test. The results demonstrate that there was an average 130-fold increase in the number of circulating CD83$^+$/HLA-DR$^+$ cells by day 7 in cohort D patients (FIG. 2B; range 26 to 399-fold increase). In addition FIG. 5 shows representative two-dimensional dot-plots (CD83 stained vs. unstained) for cohorts AI, AII, B, C and D, and the average percentage (±SEM) of PBMC expressing the CD83$^+$/HLA-DR$^+$ phenotype for that cohort is displayed numerically, * p$\leq$0.05 compared to cohort AI. Together, these results demonstrated that systemic administration of GM-CSF in combination with higher doses of IL-4 induced an increase in number of circulating CD83$^+$ cells, likely developed from stem cells, and induced an increase in the expression of CD83 and HLA-DR, in a dose and time-dependent manner in vivo.

Figure 6:
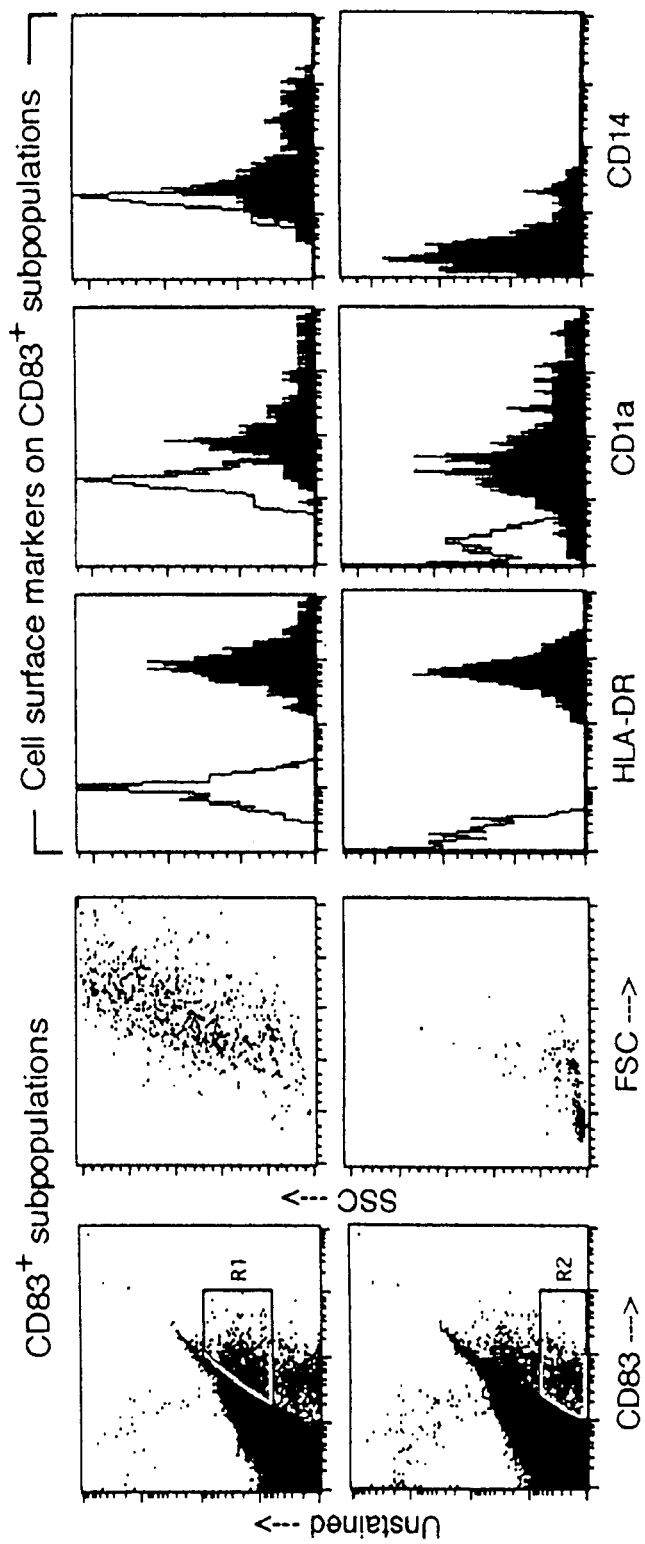

The CD83$^+$/HLA-DR$^+$ population was also examined in detail (FIG. 6). Peripheral blood leukocytes were stained with anti-CD83 in combination with either anti-HLA-DR, anti-CD1a or anti-CD14, and analyzed by FACS. Representative results for the D cohort, patient D2. Top set of graphs represents cells prior to administration of GM-CSF and IL-4. Bottom set of graphs represents cells after administering GM-CSF and IL-4. The population was comprised of two distinct subsets of cells: one containing smaller cells with minimal autofluorescence (R2 cells, FIG. 6) and the other containing larger cells with a relatively high autofluorescence (R1 cells, FIG. 6). The CD83$^+$ cells with low (R2) and high (R1) autofluorescence were analyzed individually for their size (FSC) and cellular complexity (SSC) and for their expression of CD14, CD1a and HLA-DR. Both subsets of cells expressed HLA-DR and CD1a, and neither expressed CD14; a pattern consistent with antigen presenting cells that developed from stem cells, rather than from CD 14$^+$ precursors.

Example 6

Endocytosis Assay of Antigen Presenting Cells Generated in vivo

Figure 4:
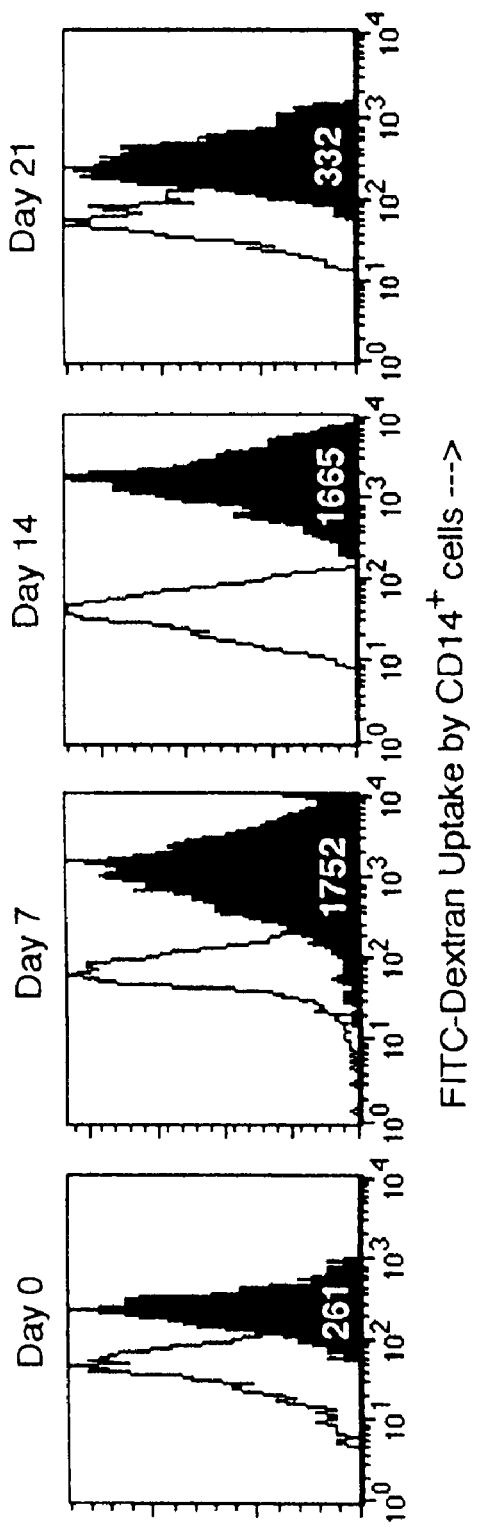
FIG. 4: Graphs showing that in vivo exposure to GM-CSF and IL-4 increased receptor mediated endocytosis.

The present invention provides a method for enhancing the development of APC by administering GM-CSF and IL-4. The development DC with antigen presenting activity is associated with an increase in the ability to take up and process antigen. As a measure of this function, CD 14$^+$ cells from cohort D patients were serially evaluated on days 0, 7, 14 and 21 for their capacity to take up FITC-labeled dextran (FIG. 4). Peripheral blood leukocytes were collected by density-gradient centrifugation and cultured for 60 minutes at either 0° C. (white histograms) or 37° C. (black histograms) in the presence of FITC-dextran (1 mg/ml). The assay was performed at both 0° C. and 37° C. in order to discriminate surface binding (occurring at 0° C.) from receptor-mediated endocytosis (occurring only at 37° C.). Cells were counter-stained with anti-CD14-PE, and the intracellular accumulation of FITC-dextran by CD14$^+$ cells was determined by FACS. FIG. 4 shows a representative analysis of patient D2, from cohort D. The results demonstrated that cells collected at days 7 and 14 of therapy exhibited a 5 to 6-fold greater uptake of FITC-dextran, when compared to CD14$^+$ cells collected from either days 0 or 21. These results demonstrated that systemic administration of GM-CSF in combination with higher doses of IL-4 induced the development of a population of circulating cells that exhibit a functional activity of APC, specifically the ability to take up antigen.

Example 7

Allogeneic MLR Assay of Antigen Presenting Cells Generated in vivo

Figure 7:
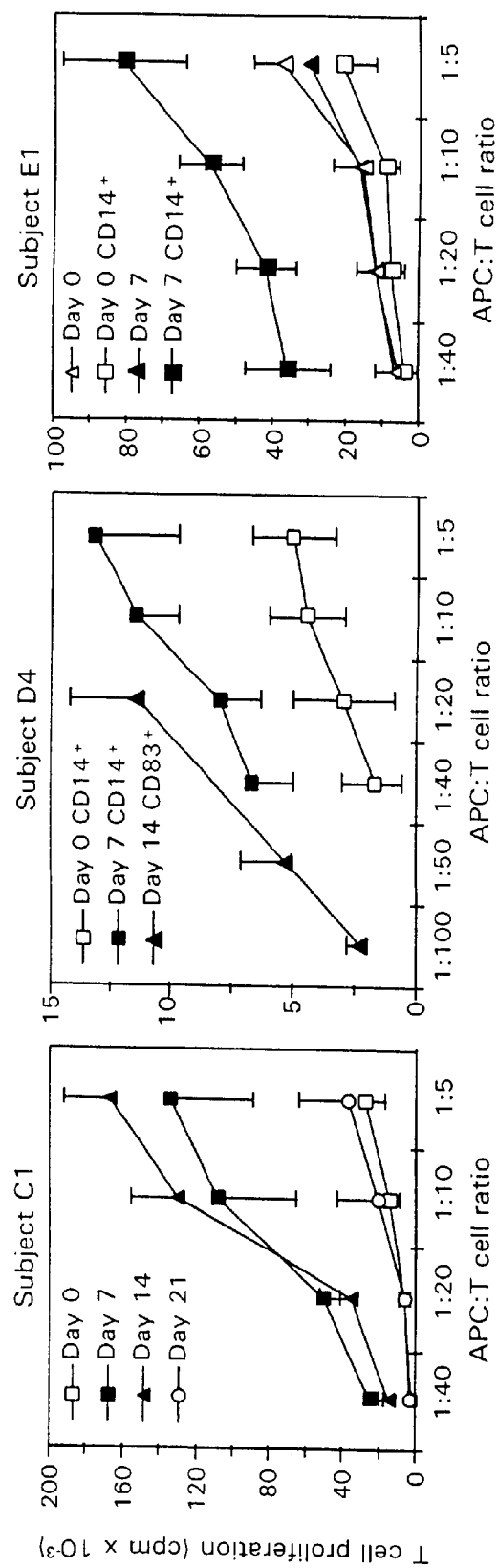
FIG. 7: Graphs showing that in vivo exposure to GM-CSF and IL-4 increased APC activity in some patients. Peripheral blood leukocytes were collected at different days, purified into different cell subsets, and assayed for their ability to stimulate T cell proliferation in an allogeneic MLR.

The present invention provides a method for enhancing the development of APC by administering GM-CSF and IL-4. The development of cells with antigen presenting activity is also associated with an increase in the ability to stimulate antigen-specific proliferation of T-cells. As a measure of this function, PBMC collected from patients in five cohorts were analyzed in an allogeneic MLR assay (FIG. 7). Peripheral blood leukocytes were collected on days 0, 7, 14 and 21 of therapy, and were depleted of contaminating neutrophils using endotoxin-free anti-CD24 mAb (2 µg/10$^6$ cells, PharMingen) in combination with immunomagnetic beads (4:1 bead:cell ratio). The PBMC were then irradiated with 30 Gy from a cesium source, and used as stimulator cells at concentrations ranging from 2.5×10$^3$ to 2×10$^4$ cell/well (these correspond to PBMC:T-cell ratios of 1:40 to 1:5 in FIG. 7, Subject C1). The stimulator cells were cultured for 6 days with 1×10$^5$ responder T-cells, pulsed with 1 µCi of [$^3$H]-thymidine/well (DuPont-NEN, Boston, Mass.), then harvested 18 hours later using an automated cell harvester (PhD cell harvester: Cambridge Technology, Cambridge, Mass.). The counts per minute (cpm) were determined by liquid scintillation counting and each data point was represented by the average ±SD of 3–6 wells. The stimulator cells from each patient, on different days of therapy, were always paired with responder T-cells prepared from the non-adherent PBMC of the same single healthy donor.

FIG. 7 shows representative data from the MLR assays of cells collected from patient C1 (cohort C, FIG. 7A), D4 (cohort D, FIG. 7B) and E1 (cohort E, FIG. 7C). For patient D4, CD14$^+$ and CD83$^+$ cell populations were isolated by cell sorting on days 0, 7 and 14, and compared for their APC activity in MLR assays. Cell sorting for CD14$^+$ cells was performed by staining with fluorescent-labeled anti-CD14 and anti-CD15 before applying to a FACStar$^{plus}$ flow cytometer (Becton Dickinson, San Jose, Calif.) using Lysys II software (Becton Dickinson, San Jose, Calif.) to recover the CD14$^+$ population. Cell sorting for CD83$^+$ cells was performed by first depleting T cells, B cells and NK cells from PBMC using murine monoclonal antibodies and immunomagnetic beads as described in Example 3 above. This depleted population was then stained with fluorescent labeled anti-CD83 and sorted on the FACStar$^{plus}$ flow cytometer. For patient E1, sorted CD14$^+$ cells from day 0 were compared to sorted CD14+cells from day 7, and both of these populations were compared to untreated peripheral blood leukocytes obtained on the same days. The results demonstrated that the cells collected from patients treated with GM-CSF alone or GM-CSF in combination with the lower doses of IL-4 (cohorts AII B) showed no consistent ability to stimulate proliferation of T-cells. However, leukocytes collected from one out of four patients in cohort C, from two out of four patients in cohort D, and from four out of four patients in cohort E demonstrated an increase in MLR stimulatory activity on days 7 and/or 14 of therapy when compared to day 0. This stimulatory activity returned to baseline by one week after cessation of cytokine therapy. Further, the sorting experiments suggested that cells expressing CD14 and/or CD83 were responsible for this increased MLR stimulatory activity. These results demonstrated that systemic administration of GM-CSF in combination with higher doses of IL-4 induced development of a population of circulating cells that exhibit a functional activity of APC, specifically the ability to stimulate proliferation of T-cells.

Example 8

Co-administration of a Tumor-associated Antigen

The present invention provides a method for stimulating a tumor-specific immune response by administering GM-CSF and IL-4, and co-administering at least one tumor-associated or tumor-specific antigen. It is postulated that the tumor-specific and/or tumor-associated antigen will be taken up by APC, thereby allowing them to stimulate an antigen-specific immune response. The present invention provides a method for co-administration of the antigen simultaneously or substantially simultaneously with GM-CSF and IL-4. Alternatively, the present invention provides a method for co-administration of the antigen sequentially, in any order with GM-CSF and IL-4. A preferred embodiment of the invention includes co-administration of at least one tumor-associated antigen.

The choice of tumor-associated antigen for use in the invention will depend upon the type of cancer to be treated. The present invention provides a method for co-administration of tumor-associated antigen including, but not limited to the following: Melan-A, tyrosinase, p97, beta-HCG, GalNAc, MAGE-1, MAGE-2, MAGE-4, MAGE-12, MART-1, MUC1, MUC2, MUC3, MUC4, MUC18, CEA, DDC, melanoma antigen gp75, Hker 8, high molecular weight melanoma antigen, K19, Tyr1 and Tyr2, members of the pMel 17 gene family, c-Met, PSA, PSM, alpha-fetoprotein, thyroperoxidase, gp100, and p185$^{neu}$. This list is not intended to be exhaustive, but merely exemplary of the different antigens that may be used in the practice of the invention.

Tumor antigens may be delivered as purified proteins, peptides, or gene-based vaccines in the presence or absence of an appropriate carrier or adjuvent. Dose ranges for antigen delivery will depend upon the type of antigen, the route of administration, and other factors to be determined according to protocols standard to the art of antigen vaccination.

What is claimed is:

1. A method for enhancing the in vivo development of the number and function of a population of antigen presenting precursor cells expressing CD14 or CD11c within peripheral blood in a human, the method comprising:

administering GM-CSF and IL-4 in vivo simultaneously so as to enhance development of the number and function of circulating peripheral blood antigen presenting precursor cells.

2. The method of claim 1, wherein administration of GM-CSF and IL-4 is effected systemically or locally.

3. The method of claim 2, wherein local administration of GM-CSF and IL-4 is effected by local injection.

4. The method of claim 2, wherein systemic administration of GM-CSF and IL-4 is effected by a delivery system selected from the group consisting of implantable pump, continuous infusion, gene therapy, lipososomes, and injection.

* * * * *